US00PP15627P3

(12) United States Plant Patent
Sanders

(10) Patent No.: US PP15,627 P3
(45) Date of Patent: Mar. 8, 2005

(54) *AGERATUM* PLANT NAMED 'AGETIS'

(50) Latin Name: *Ageratum houstonianum*
Varietal Denomination: Agetis

(75) Inventor: Monica M. A. Sanders, Grootebroek (NL)

(73) Assignee: Syngenta Seeds B.V., Enkhuizen (NL)

( * ) Notice: Subject to any disclaimer, the term of this patent is extended or adjusted under 35 U.S.C. 154(b) by 182 days.

(21) Appl. No.: 10/045,978

(22) Filed: Jan. 10, 2002

(65) Prior Publication Data

US 2003/0131389 P1 Jul. 10, 2003

(51) Int. Cl.[7] ..... A01H 5/00

(52) U.S. Cl. ..... Plt./263
(58) Field of Search ..... Plt./263

(56) References Cited

PUBLICATIONS

GTITM UPOVROM Citation for 'Agetis' as per QZ PBR 001592; Oct. 27, 2000.*

* cited by examiner

*Primary Examiner*—Kent Bell
(74) *Attorney, Agent, or Firm*—Bruce Vrana; Edouard Lebel

(57) ABSTRACT

A new *Ageratum* plant particularly distinguished by its large blue flower, early flowering, nicely branched plant habit and vigorous growth.

1 Drawing Sheet

Latin name of the genus and species of the plant claimed: *Ageratum houstonianum.*
Variety denomination: 'Agetis'.

BACKGROUND OF THE NEW PLANT

The present invention comprises a new distinct cultivar of *Ageratum,* botanically known as *Ageratum houstonianum.* The new cultivar is propagated from cuttings resulting from the cross of 'Q343-2' and 'S570-2'. 'Q343-2' is a purple flowering *Ageratum* having a compact habit. 'Q343-2' is not commercially available and is not known by any synonyms. 'S570-2' is a blue and white flowering *Ageratum* having an upright habit. 'S570-2' is a selection from the variety 'Southern Cross'.

Neither 'Q342-2' or 'S570-2' has been patented. As a result of this cross the present cultivar was created in 1997 in Enkhuizen, Netherlands and has been repeatedly asexually reproduced by cuttings in Enkhuizen, Netherlands, in Gilroy, USA, in Angers, France and in Sarrians, France over a three-year period. The distinctive characteristics of this new *Ageratum* are stable and reproduced true to type in successive generations of asexual reproduction. It takes 9 to 11 weeks to produce a finished plant, depending on the temperature.

This new *Ageratum* plant is an annual in most climatical zones in the US, only in zones 9 and 10 is it a perennial plant.

DESCRIPTION OF THE DRAWING

This new *Ageratum* plant is illustrated by the accompanying photographic drawing which shows blooms, buds and foliage of the plant in full color, the color shown being as true as can be reasonably obtained by conventional photographic procedures.

DESCRIPTION OF THE NEW CULTIVAR

The following detailed descriptions set forth the distinctive characteristics of this new *Ageratum.* The data which defines these characteristics were collected from asexual reproductions carried out in Enkhuizen, Netherlands. The plant history was taken on 20 weeks old plants, blossomed under natural light and artificial light in a greenhouse. Color readings were taken in the greenhouse under ambient light. Color references are primarily to The R.H.S. Color Chart of The Royal Horticultural Society of London.

TABLE 1

Differences between the new variety 'Agetis', its parents and a similar cultivar

| Character | 'Agetis' | 'Q343-2' | 'S570-2' | 'R116' |
|---|---|---|---|---|
| Flower color | Violet | Purple | Blue and white | Violet |
| Size of capitulum | 16–21 mm | 6–9 mm | 16–21 mm | 7–9 mm |
| Plant height | 30–40 cm | 20–25 cm | 25–35 cm | 20–25 cm |
| Branching | At every internode | At every internode | Not at every internode | At every internode |

THE PLANT

Classification — Botanical: *Ageratum houstonianum.*
Parentage:

*Female parent.*—A seedling named 'Q343-2' is one of our seedlings from our Q-generation of plants bred in 1987.

*Pollen parent.*—A seedling named 'S570-2' is one of our seedlings from our S-generation of plants bred in 1997.

Growth habit: Erect, well branched.
Plant height: 30–40 cm.
Spreading area of plant: 30–40 cm.
Growth rate: Vigorous.
Strength: Very good.

Branching character: Freely branching and lateral branching at every node.
Blooming period: Year round.

THE STEM

Diameter: 2–2.5 mm.
Shape: Round.
Color: 145B.
Anthocyan pigmentation: Absent.
Length of the stems: 11–40 cm.
Length of the internodes: 30–42 mm, depending on the light where the plant is propagate.
Pubescence: Slightly pubescent.

THE FOLIAGE

Phyllotaxis: Opposite, decussate.
Shape of blade: Ovate.
Texture:
*Upper side.*—Slightly pubescent.
*Lower side.*—Slightly pubescent.
Venation: Reticulate.
Leaf margin: Crenate.
Leaf base: Cordate.
Leaf apex: Rounded.
Length: 27–63 mm.
Width: 30–68 mm.
Color:
*Upper side.*—Dark green 137A.
*Lower side.*—Medium green 143A.
Pubescence: Some pubescence is present.
Length of petiole: 11–15 mm.
Color of petiole: Light green 145C.
Petiole surface texture: Slightly pubescent.

INFLORESCENSE

Inflorescense: Compound umbel of capitula.
Length of peduncle: 18–35 mm.
Diameter of peduncle: 2–3 mm.
Color of peduncle exposed to light: RHS 152B.
Color of peduncle not exposed to light: RHS145A.
Length of pedicel: 4–11 mm.
Diameter of pedicel: 1–2 mm.
Color of pedicel: RHS 145A.
Number of inflorescence per plant: 5–9 when ready for sale.
Diameter of umbel: 4–6 cm.
Depth of umbel: 2–5 cm.
Number of capitula per inflorescense: 10–19.
Number of disc florets per capitulum: 80–120.
Capitulum in bud stage bud: Round, flat capitulum, showing unopened florets from the start.
Number of ray florets: 0.
Shape of corolla of the disk floret: Actinomorph.
Number of lobes: 5.
Length of disc floret: 4–5 mm.
Diameter of disc floret: 1–2 mm.
Color of disc floret upper side: RHS 083D.
Color of disc floret lower side: RHS 157D.
Number of phyllaries per capitulum: 23–25.
Length of phyllary: 4–5 mm.
Diameter of phyllary: 1–2 mm.
Color of upper side of phyllary: RHS 143A.
Color of lower side of phyllary: RHS 143B.
Diameter of capitulum at beginning of flowering: 7–8 mm.
Depth of capitulum: 6–8 mm.
Color of capitulum at beginning of flowering: RHS 083D.
Diameter of capitulum at full flowering: 16–21 mm.
Color of capitulum at full flowering: RHS 086D.

REPRODUCTIVE ORGANS

Number of pistels: 1.
Shape of pistels: Style with two filiform branches.
Length of stigma and style: 8–9 mm.
Color of stigma: RHS 091A.
Inferior ovary: 5-ribbed.
Pappus: Short.
Number of anthers: 5, connate in a tube, filaments free.
Shape of anthers: Ecalcarate.
Pollen: No pollen is produced.
Fragrance: No fragrance.
Lastingness of the bloom: The capitula of one umbel open over a period of 5 to 6 weeks.

SEEDS

Seedset: No seedset has been observed.

ROOTS

Type of roots: Fibrous. Roots start to grow on every part of the stem that contacts the soil, so not only at the nodes.

PHYSIOLOGICAL AND ECOLOGICAL CHARACTERISTICS

Good tolerance to heat and cold, but no frost tolerance. Strong resistance to pests and diseases.

What is claimed is:

1. A new and distinct variety of *Ageratum* plant, substantially as herein illustrated and described, characterized particularly as to novelty by big blue flowers, which appear early on the plant, which produces no seeds, and has a growing habit that is erect, well branched and vigorous.

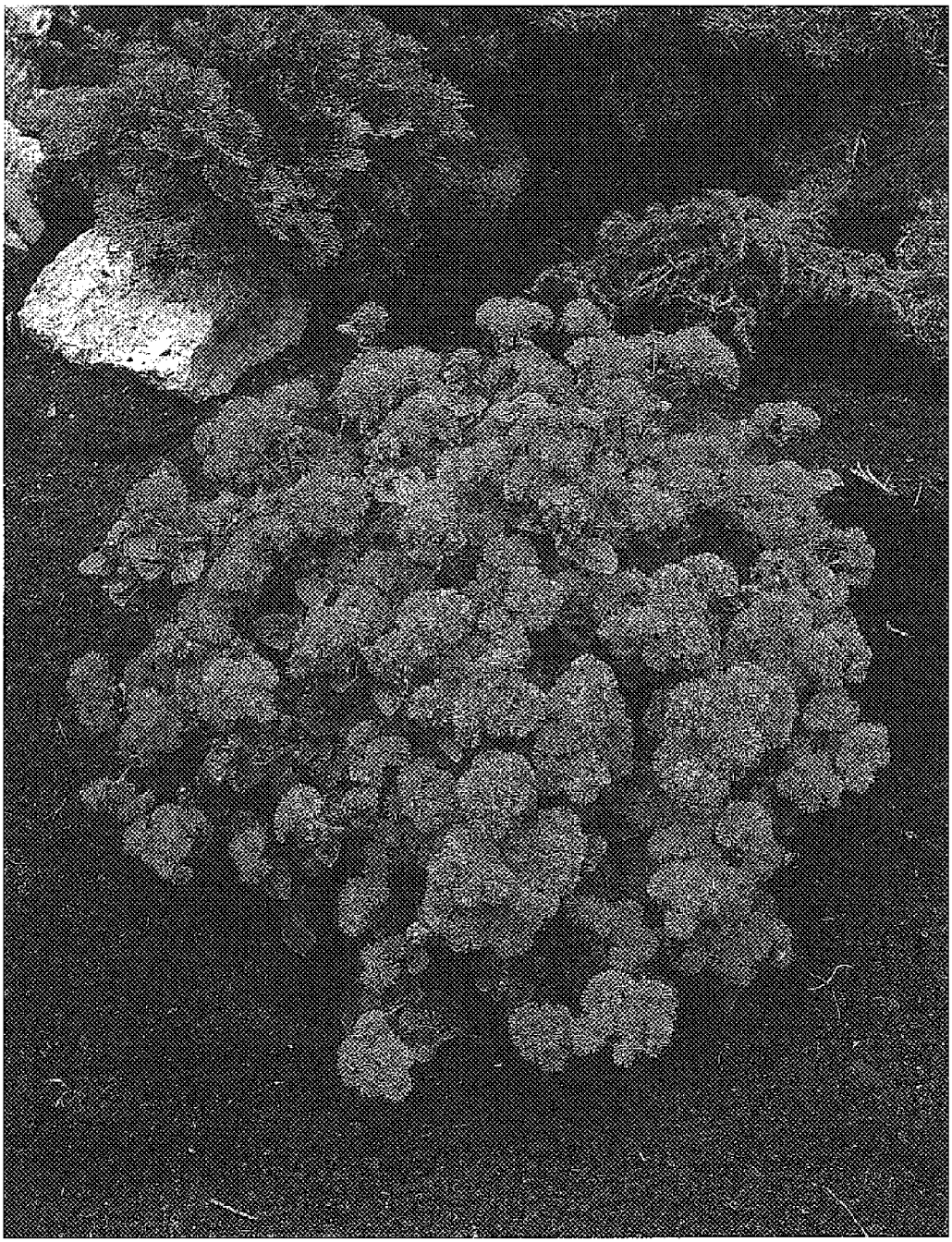

* * * * *